United States Patent [19]

Fust

[11] 4,029,096
[45] June 14, 1977

[54] FOOT POWDER DISPENSING DEVICE

[76] Inventor: George Fust, 44 Kunigunda Place, Islip Terrace, N.Y. 11752

[22] Filed: Aug. 3, 1976

[21] Appl. No.: 711,257

[52] U.S. Cl. .............................. 128/265; 222/193
[51] Int. Cl.² ....................................... A61M 35/00
[58] Field of Search .......... 128/265, 266, 260, 588; 222/179, 193, 194; 239/8

[56] References Cited
UNITED STATES PATENTS

| | | | |
|---|---|---|---|
| 2,484,659 | 10/1949 | Swerdlow et al. ................. | 128/265 |
| 3,130,726 | 4/1964 | Rich ................................. | 128/265 |

*Primary Examiner*—Robert W. Michell
*Assistant Examiner*—Michael H. Thaler
*Attorney, Agent, or Firm*—Joel Halpern

[57] ABSTRACT

A foot powder dispensing device includes a housing which is open at one end thereof for reception of a person's foot and is adapted adjacent its other end to support a foot powder container so that the lower discharge end of the container extends into the housing. A treadle element is provided which is pivotably supported at one end thereof by an apertured base of the housing. The treadle element is spring biased upwardly adjacent its other end. An upstanding apertured wall is located within the housing adjacent the free end of the treadle element to thereby define, together with the inner adjacent surfaces of the housing, a powdering chamber. Depression of the treadle element by one's foot forces a stream of air into the powdering chamber and entrains a quantity of powder therein for application to and between the toes of the foot.

5 Claims, 3 Drawing Figures ical to the invention.

FOOT POWDER DISPENSING DEVICE

BACKGROUND OF THE INVENTION

The present invention relates to foot powder dispensing devices and more particularly to a device which is foot actuable and includes a housing into which the foot is inserted for dusting.

Foot powder dispensing devices have been known heretofore. U.S. Pat. No. 2,484,659 issued Oct. 11, 1949 to M. H. Swerdlow et al discloses a device in which a treadle element is hingedly mounted within a casing and supports a depending resilient container for the foot powder. Depression of the treadle element by the foot compresses the resilient container and forces powder and air out of the container for dusting of the foot. However, since the container is disposed below the treadle element the depression of the treadle element tends to create back pressure within the container which to varying degrees interferes with the dusting function and also compacts the powder within the container resulting in caking of the powder and decreased operativeness of the device.

SUMMARY OF THE INVENTION

It is one object of the invention to provide a foot powder dispensing device which is foot actuable and capable of maintaining its effectiveness over prolonged periods of use.

Another object of the invention is the provision of a foot powder dispensing device which is foot actuable and so constructed that the foot powder dispensed is confined within the housing of the device.

Still another object of the invention is the provision of a foot powder dispensing device which is foot actuable and provides for support of the foot powder container and air-generating mechanism so as to avoid compacting or caking of the powder within the container.

Other objects and advantages of the invention will become readily apparent from the following description of the invention.

According to the present invention there is provided a foot powder dispensing device comprising in combination a housing open at one end thereof for reception of a foot and including a base having a plurality of apertures therein; a substantially air-impermeable treadle element pivotably mounted at one end thereof on said base within said housing; a spring member interposed between said base and said treadle element and adapted to bias the free end of such treadle element upwardly, an upstanding wall having a plurality of apertures therein positioned within said housing adjacent and free end of said treadle element and defining together with the surrounding inner surfaces of said housing a powdering chamber; an opening adjacent the other end of said housing adapted to receive and support a container for foot powder; means for selectively effecting communication between the container and said powdering chamber; whereby actuation of said treadle element by a foot effects the flow of a stream of air through said apertured wall and into said powdering chamber and the entrainment of a quantity of foot powder therein and the application of the powder-laden air to and between the toes of the foot.

BRIEF DESCRIPTION OF THE DRAWINGS

In order that the invention may be more fully comprehended it will now be described, by way of example, with reference to the accompanying drawings in which.

DETAILED DESCRIPTION OF THE PREFERRED EMBODIMENT

Figure 2:
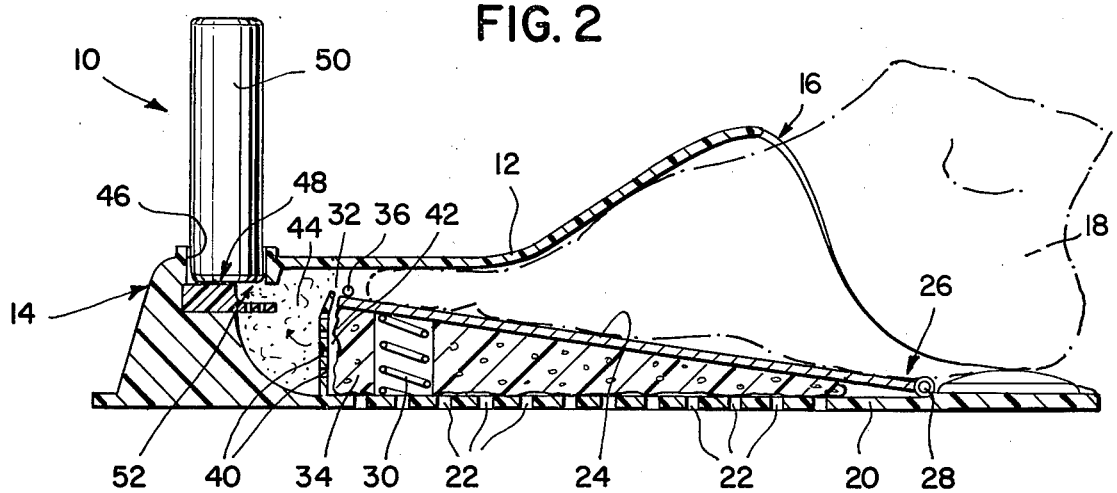
FIG. 2 is a side elevational view, partly in cross-section, of the foot powder dispensing device shown in FIG. 1 taken along line 2—2 thereof.
Figure 1:
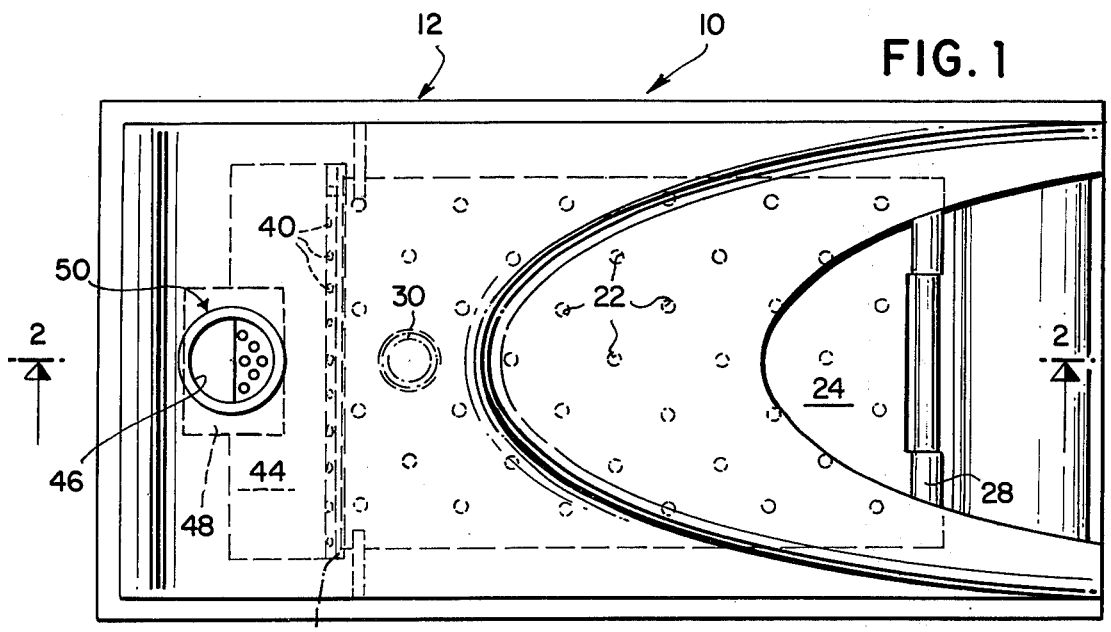
FIG. 1 is a top plan view of a foot powder dispensing device embodying the features of the invention.

Referring to the drawings there is shown generally, as indicated by reference numeral 10, a foot powder dispensing device which is foot actuable.

The device comprises a housing 12 which is configured generally in the shape of a shoe or slipper so as to provide a toe portion 14 at one end thereof and an open portion 16 at the other end thereof dimensioned to receive the foot 18 of a person for dusting with a foot powder. Such foot powder may consist of any of the known compositions and may be medicated. The housing includes a base 20 which is given a plurality of apertures 22 which extend therethrough for a purpose which will become clear.

A treadle element 24 is mounted pivotably within the housing such as by being hingedly connected adjacent one end 26 thereof to the base 20 by means of a pivot pin 28. It will be understood, however, that the specific construction employed for the pivotal connection between the treadle element and the base is not critical to the invention.

A spring member 30 is interposed between the treadle element and the base so as to bias the free end 32 of the treadle element upwardly. Preferably a sponge member 34 is positioned in the space between the treadle element and base. Such sponge member should be porous so as to permit air to permeate same through apertures 22. If desired a stop member 36 may be provided on the upper surface of the free end of the treadle element in order to limit the upward movement thereof under the influence of spring 30. However, it is generally sufficient to select a spring with a spring constant such that the treadle element is not urged upwardly into engagement with the overlying surface of the housing.

An upstanding wall 38 is positioned within the housing and may be formed integrally with base 20. The wall is provided with a plurality of apertures 40 communicating the space 42 between the treadle element and base with a powdering chamber 44 defined by wall 38 and the surrounding inner surface of the housing. It will thus be seen that depression of the treadle element causes a stream of air to flow through the apertured wall 38 into the powdering chamber 44.

The housing 12 is provided with an opening 46 in the toe portion thereof. Within the opening there is formed a support ledge 48 which is dimensioned to preferably extend across approximately one half the lateral extent of the opening. A foot powder container 50 is positionable within the opening 46 so as to be supported by the ledge 48. The container is of the type which is given powder discharge means such as one or more apertures in the lower end 52 thereof. As will be understood, the container is rotatably mounted on the ledge such that it may be selectively rotated between a first position in which the ledge acts as a valve plate to prevent the discharge of powder from the container and a second position in which the apertures of the container are exposed within the area of the opening 46 which is not covered by the ledge. In such latter position there is open communication between the container and the powdering chamber via the apertures of the container. Actuation of the treadle element with the container in such latter position results in the entrainment of powder in the air blown through the apertured wall 38 and the application of the powder to and between the toes of the foot.

Figure 3:
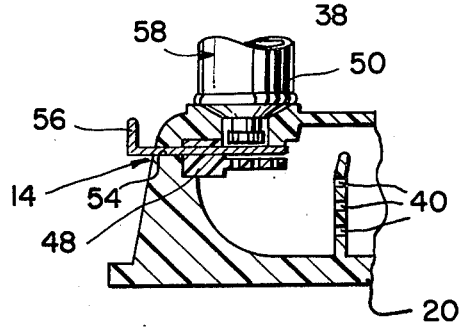
FIG. 3 is a view similar to that of FIG. 2 showing a different arrangement for support of the foot powder container.

FIG. 3 illustrates a modified arrangement for support of the foot powder container. In accordance with this embodiment of the invention the ledge 48 may be apertured, and a slot 54 formed in the toe of the housing. A slide valve 56 is slidably mounted in the slot and is selectively movable so as to close the apertures in the ledge to thereby prevent communication between the foot powder container 50 and the powdering chamber 44. The upper end 58 of the container is adapted to be opened when refilling of same is required. The foot powder container according to this embodiment is a part of the device and is not the conventional container in which the foot powder is sold. It will be understood also that instead of the ledge 48 being apertured the lower end of the container may be apertured and a construction employed for support thereof upon the ledge such that a space is provided between portions of the ledge and container to afford the required communication between the container and the powdering chamber. The slide valve 56 thus serves to selectively open or close the apertures in the container.

From the foregoing it will be seen that a foot powder dispensing device has been provided which is relatively simple in construction and which will reliably provide the desired powder dusting of the foot without risk of compaction of the powder within the container through actuation of the treadle element. Further, due to the construction which effects the admission of air and the entrainment of foot powder therein for application to the toes of the foot there is no interference either with the admission of air or with the entrainment of powder within such air or in the distribution of the powder-laden air over the surface of the foot to be treated.

I claim:

1. A foot powder dispensing device comprising in combination:

a housing open at one end thereof for reception of a foot and including a base having a plurality of apertures therein;

a substantially air-impermeable treadle element pivotably mounted at one end thereof on said base within said housing;

a spring member interposed between said base and said treadle element and adapted to bias the free end of such treadle element upwardly;

an upstanding wall having a plurality of apertures therein positioned within said housing adjacent the free end of said treadle element and defining together with the surrounding inner surfaces of said housing a powdering chamber;

an opening adjacent the other end of said housing adapted to receive the support a container for foot powder; means for selectively effecting communication between the container and said powdering chamber; whereby actuation of said treadle element by a foot effects the flow of a stream of air through said apertured wall and into said powdering chamber and the entrainment of a quantity of foot powder therein and the application of the powder-laden air to and between the toes of the foot.

2. A foot powder dispensing device according to claim 1, wherein a porous sponge is positioned within the space between said treadle element and said base.

3. A foot powder dispensing device according to claim 1, wherein said housing is adapted to support the foot powder container rotatably within said opening.

4. A foot powder dispensing device according to claim 3, wherein said means for selectively effecting communication is a ledge provided to support the lower end of the container, said ledge being dimensioned to extend across approximately one half the lateral extent of said opening, whereby the container may be selectively rotated between a first position in which the discharge end thereof is in communication with said powdering chamber and a second position in which said ledge acts as a valve plate to prevent communication between the discharge end of the container and said powdering chamber.

5. A foot powder dispensing device according to claim 1, wherein said means for selectively effecting communication is a slot provided in said other end of said housing and a slide valve slidably positioned in said slot and extendable across the discharge end of the container to selectively effect communication between the discharge end of the container and said powdering chamber, the upper end of the container being adapted to be opened to allow refilling of the container with foot powder when desired.

* * * * *